United States Patent
Suenaga et al.

(10) Patent No.: US 10,066,058 B2
(45) Date of Patent: Sep. 4, 2018

(54) POLYIMIDE RESIN

(71) Applicant: MITSUBISHI GAS CHEMICAL COMPANY, INC., Tokyo (JP)

(72) Inventors: Shuya Suenaga, Kanagawa (JP); Teruhisa Matsumaru, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 108 days.

(21) Appl. No.: 14/899,222

(22) PCT Filed: Jul. 3, 2014

(86) PCT No.: PCT/JP2014/067814
§ 371 (c)(1),
(2) Date: Dec. 17, 2015

(87) PCT Pub. No.: WO2015/002273
PCT Pub. Date: Jan. 8, 2015

(65) Prior Publication Data
US 2016/0137789 A1    May 19, 2016

(30) Foreign Application Priority Data
Jul. 5, 2013    (JP) .................................. 2013-141585

(51) Int. Cl.
*C08G 73/10* (2006.01)
*C08K 3/36* (2006.01)
(Continued)

(52) U.S. Cl.
CPC .......... *C08G 73/1082* (2013.01); *B32B 9/045* (2013.01); *B32B 15/08* (2013.01);
(Continued)

(58) Field of Classification Search
CPC ... C09D 179/08; C08L 79/08; C08G 73/1042; C08J 2379/08
See application file for complete search history.

(56) References Cited

U.S. PATENT DOCUMENTS

| | | | | |
|---|---|---|---|---|
| 6,392,004 B1 * | 5/2002 | Chien | .................... | C08G 73/10 343/700 R |
| 8,927,678 B2 * | 1/2015 | Sato | ....................... | C08G 73/10 428/458 |

(Continued)

FOREIGN PATENT DOCUMENTS

| | | |
|---|---|---|
| CN | 101959935 | 1/2011 |
| JP | 11-012465 | 1/1999 |

(Continued)

OTHER PUBLICATIONS

English-language machine translation of JP 2013-82774 to Kikuzawa. Obtained from the AIPN/JPO website on Aug. 21, 2017.*

(Continued)

*Primary Examiner* — Michael A Salvitti
(74) *Attorney, Agent, or Firm* — Greenblum & Bernstein, P.L.C.

(57) ABSTRACT

A polyimide resin contains repeating structural units represented by formulas (1) and (2), wherein the content of the repeating structural unit represented by formula (2) relative to the total of the repeating structural unit represented by formula (1) and the repeating structural unit represented by formula (2) falls within a specific range and the content of the divalent group represented by the following structural formula (B1) falls within a specific range:

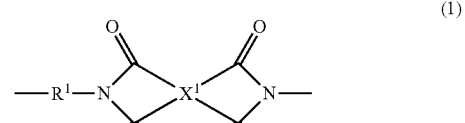

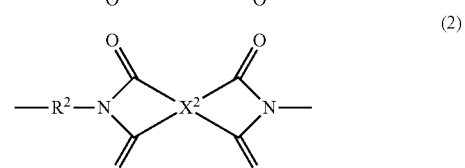

$X^1$ represents a tetravalent group containing an alicyclic hydrocarbon structure and having a carbon number of from 4 to 22. $X^2$ represents a tetravalent group containing an aromatic ring and having a carbon number of from 6 to 22. $R^1$ and $R^2$ each independently represent a divalent organic group, and the content of the divalent group represented by the following structural formula (B1) relative to the total of $R^1$ and $R^2$ is from 80 to 100 mol %:

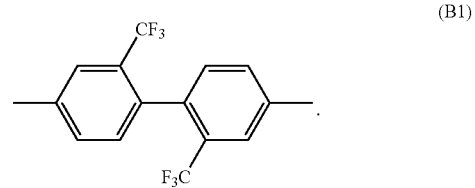

18 Claims, No Drawings

(51) Int. Cl.

| | | |
|---|---|---|
| *C09D 179/08* | (2006.01) | |
| *B32B 15/08* | (2006.01) | |
| *B32B 27/08* | (2006.01) | |
| *B32B 27/28* | (2006.01) | |
| *C08J 5/18* | (2006.01) | |
| *B32B 9/04* | (2006.01) | |
| *B32B 17/06* | (2006.01) | |
| *C07C 235/82* | (2006.01) | |
| *C07C 235/84* | (2006.01) | |

(52) U.S. Cl.
CPC ............ *B32B 17/064* (2013.01); *B32B 27/08* (2013.01); *B32B 27/281* (2013.01); *C07C 235/82* (2013.01); *C07C 235/84* (2013.01); *C08G 73/1039* (2013.01); *C08G 73/1042* (2013.01); *C08G 73/1078* (2013.01); *C08J 5/18* (2013.01); *C08K 3/36* (2013.01); *C09D 179/08* (2013.01); *B32B 2250/02* (2013.01); *B32B 2307/306* (2013.01); *B32B 2307/412* (2013.01); *B32B 2457/14* (2013.01); *B32B 2457/20* (2013.01); *B32B 2551/00* (2013.01); *C08J 2379/08* (2013.01)

(56) References Cited

U.S. PATENT DOCUMENTS

| | | | |
|---|---|---|---|
| 9,073,297 B2* | 7/2015 | Suenaga | B32B 33/00 |
| 9,670,320 B2* | 6/2017 | Sato | C08G 73/1028 |
| 2003/0220455 A1* | 11/2003 | Ichiroku | C08G 59/18 |
| | | | 525/418 |
| 2007/0009751 A1 | 1/2007 | Hwang et al. | |
| 2008/0090927 A1 | 4/2008 | Ishii et al. | |
| 2011/0111333 A1* | 5/2011 | Cheng | G02B 5/201 |
| | | | 430/7 |
| 2013/0178597 A1 | 7/2013 | Takawasa et al. | |
| 2014/0322444 A1* | 10/2014 | Suenaga | B32B 33/00 |
| | | | 427/248.1 |
| 2015/0225523 A1* | 8/2015 | Suenaga | C08G 73/1039 |
| | | | 428/435 |
| 2016/0137789 A1* | 5/2016 | Suenaga | C08G 73/1042 |
| | | | 428/220 |

FOREIGN PATENT DOCUMENTS

| | | | |
|---|---|---|---|
| JP | 2006-70096 | | 3/2006 |
| JP | 2008-214413 | | 9/2008 |
| JP | 2009-215412 | | 9/2009 |
| JP | 2010-202729 | | 9/2010 |
| JP | 2011-148955 | | 8/2011 |
| JP | 2012-41530 | | 3/2012 |
| JP | 2013-82774 | * | 5/2013 |
| TW | 200626636 | | 8/2006 |
| TW | 200702357 | | 1/2007 |
| WO | 2009/107429 | | 9/2009 |
| WO | 2012/011590 | | 1/2012 |
| WO | 2013/024849 | | 2/2013 |

OTHER PUBLICATIONS

Inernational Search Report issued in Patent Application No. PCT/JP2014/067814, dated Oct. 7, 2014.

Extended European Search Report issued in Patent Application No. 14820576.8, dated Feb. 1, 2017.

Taiwanese Office Action issued in Counterpart Patent Appl. No. 103123234, dated Sep. 14, 2017.

* cited by examiner

POLYIMIDE RESIN

TECHNICAL FIELD

The present invention relates to a polyimide resin. More specifically, the present invention relates to a polyimide resin capable of forming a polyimide film excellent in transparency and heat resistance and having a low coefficient of linear thermal expansion.

BACKGROUND ART

Recently, with the advent of a highly information-based society, materials satisfying both heat resistance and transparency have become desired in the field of optical communications including optical fibers, optical waveguides, etc., and in the field of display devices including liquid-crystal orientation films, color filters, etc.

In the field of display devices, an alternative technology of employing plastic substrates that are lightweight and are excellent in flexibility, in place of glass substrates, and a development of displays capable of being bent or rolled up are now under way. However, for example, when an electronic element composed of an inorganic material is formed on a film, the film having the inorganic element formed thereon may bend and, as the case may be, the inorganic element may often peel away from the film, since the inorganic material and the film significantly differ in point of the linear expansion coefficient. Accordingly, it is desired to develop a resin material for films having both transparency and heat resistance and having a low coefficient of linear thermal expansion.

Polyimide has excellent heat resistance and additionally has other excellent properties of mechanical characteristics, chemical resistance, electric characteristics and the like, and therefore films formed of a material of polyimide are widely used in various fields of molding materials, composite materials, electric and electronic components, display devices, etc. However, those films are further required to have higher transparency and dimensional stability than ever.

In general, it is known that polyimides having the polymer chains which are more rigid and have a higher linearity have a lower coefficient of linear thermal expansion, and for improving the dimensional stability of polyimides by lowering the coefficient of linear thermal expansion thereof, various structures of both acid dianhydrides and diamines that are raw materials of polyimides have heretofore been proposed.

PTL 1 discloses a polyimide precursor to be formed through reaction of a diamine component containing a fluorine-containing aromatic diamine and a specific aliphatic diamine, and an acid dianhydride component containing an aliphatic tetracarboxylic dianhydride and an aromatic tetracarboxylic dianhydride. However, the polyimide film formed from the polyimide precursor has a light transmittance at a wavelength of 400 nm of 80% or so when the thickness thereof is 10 μm, that is, the film could not be said to have good transparency.

PTL 2 discloses a polyimide film formed by casting a solution prepared by mixing a solution of a specific polyamic acid having an aromatic ring with a solution containing a dehydrating catalyst and an imidating agent having a boiling point of not higher than 180° C., onto a support, and says that the film is excellent in heat resistance and has a low linear expansion coefficient. However, the polyimide film has a YI index of 15 or so when having a thickness of 50 μm, that is, the yellowness of the film is strong, and the transparency thereof is expected to be insufficient.

PTL 3 discloses a copolyimide having a biphenyl structure and having excellent transparency, high heat resistance, a high glass transition temperature, a low coefficient of linear thermal expansion and good bending resistance. However, the film formed of the copolyimide has a light transmittance at a wavelength of 400 nm of at most 80% or so, when having a thickness of 10 μm, that is, the film could not be said to have good transparency.

CITATION LIST

Patent Literature

PTL 1: WO2009/107429
PTL 2: JP-A 2011-148955
PTL 3: JP-A 2012-41530

SUMMARY OF INVENTION

Technical Problem

An object of the present invention is to provide a polyimide resin capable of forming a polyimide film which is excellent in transparency and has heat resistance and a low coefficient of linear thermal expansion.

Solution to Problem

The present inventors have found that the above-mentioned problems can be solved by a polyimide resin that contains a combination of specific repeating structural units in a predetermined ratio, thereby completing the present invention.

Specifically, the present invention relates to the following [1] to [5]:

[1] A polyimide resin containing a repeating structural unit represented by the following general formula (1) and a repeating structural unit represented by the following general formula (2), wherein the content of the repeating structural unit represented by the general formula (2) relative to the total of the repeating structural unit represented by the general formula (1) and the repeating structural unit represented by the general formula (2) is from 35 to 75 mol %.

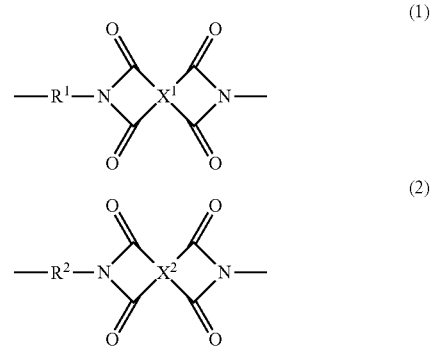

$X^1$ represents a tetravalent group containing an alicyclic hydrocarbon structure and having a carbon number of from 4 to 22. $X^2$ represents a tetravalent group containing an aromatic ring and having a carbon number of from 6 to 22. $R^1$ and $R^2$ each independently represent a divalent organic group, and the content of the divalent group represented by the following structural formula (B1) relative to the total of $R^1$ and $R^2$ is from 80 to 100 mol %.

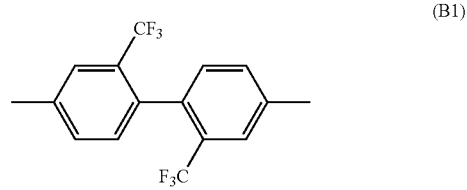

(B1)

[2] A polyamide acid that is a precursor of the polyimide resin of the above [1].

[3] A resin composition containing the polyimide resin of the above [1] and silica microparticles.

[4] A polyimide film containing the polyimide resin of the above [1].

[5] A laminate containing a substrate selected from plastic film, silicon wafer, metal foil and glass, and a polyimide resin layer containing the polyimide resin of the above [1].

Advantageous Effects of Invention

The polyimide resin of the present invention is excellent in transparency and heat resistance and has a low coefficient of linear thermal expansion, and is therefore favorable for films for members that are especially required to have dimensional stability. For example, the resin is expected to be used for color filters, flexible displays, semiconductor parts, optical members, etc.

DESCRIPTION OF EMBODIMENTS

Polyimide Resin

The polyimide resin of the present invention is a polyimide resin that contains a repeating structural unit represented by the following general formula (1) and a repeating structural unit represented by the following general formula (2), wherein the content of the repeating structural unit represented by the general formula (2) relative to the total of the repeating structural unit represented by the general formula (1) and the repeating structural unit represented by the general formula (2) is from 35 to 75 mol %.

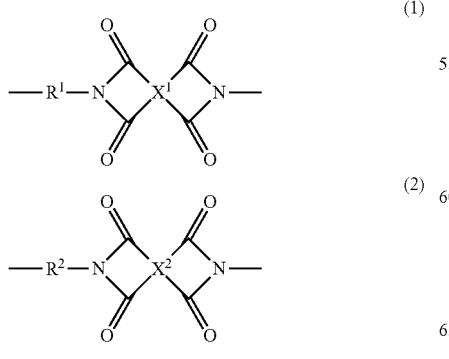

(1)

(2)

$X^1$ represents a tetravalent group containing an alicyclic hydrocarbon structure and having a carbon number of from 4 to 22. $X^2$ represents a tetravalent group containing an aromatic ring and having a carbon number of from 6 to 22. $R^1$ and $R^2$ each independently represent a divalent organic group, and the content of the divalent group represented by the following structural formula (B1) relative to the total of $R^1$ and $R^2$ is from 80 to 100 mol %.

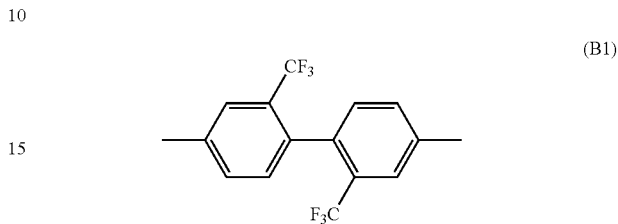

(B1)

The polyimide resin of the present invention contains a repeating structural unit represented by the above-mentioned general formula (1).

In the general formula (1), $X^1$ represents a tetravalent group containing an alicyclic hydrocarbon structure and having a carbon number of from 4 to 22. Having $X^1$ that contains an alicyclic hydrocarbon structure, the polyimide resin of the present invention is especially excellent in transparency and has heat resistance and a low coefficient of linear thermal expansion. The alicyclic hydrocarbon structure may be saturated or unsaturated, but is preferably a saturated alicyclic hydrocarbon structure from the viewpoint of the transparency.

$X^1$ may have at least one alicyclic hydrocarbon structure. Examples of the alicyclic hydrocarbon structure includes a cycloalkane ring such as a cyclobutane ring, a cyclopentane ring, a cyclohexane ring, etc., a cycloalkene ring such as a cyclohexene, etc., a bicycloalkane ring such as a norbornane ring, etc., a bicycloalkene ring such as a norbornene, etc. Of those, preferred are a cycloalkane ring and a bicycloalkane ring, more preferred are a cycloalkane ring and a bicycloalkane ring having a ring carbon number of from 4 to 6, even more preferred are a cyclohexane ring and a bicyclohexane ring, and still more preferred is a cyclohexane ring.

The carbon number of $X^1$ is from 4 to 22, preferably from 4 to 18, and more preferably from 6 to 16. From the viewpoint of the transparency of the polyimide resin, $X^1$ is preferably composed of an alicyclic hydrocarbon structure alone.

From the viewpoint of the transparency, the heat resistance and the low coefficient of linear thermal expansion of the polyimide resin, $X^1$ is preferably at least one selected from tetravalent groups represented by the following general formulae (X1-1) and (X1-2), and is more preferably a tetravalent group represented by the following general formula (X1-1).

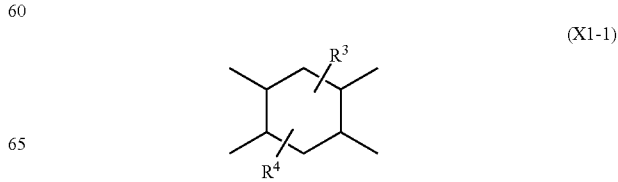

(X1-1)

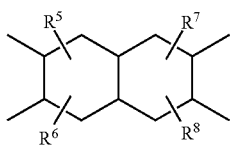
(X1-2)

$R^3$ to $R^8$ each independently represent a hydrogen atom, a halogen atom, an alkyl group having a carbon number of from 1 to 6, or a halogenoalkyl group.

In the general formulae (X1-1) and (X1-2), $R^3$ to $R^8$ each are preferably a hydrogen atom or a methyl group, and more preferably a hydrogen atom. $X^1$ is more preferably a tetravalent group represented by the following structural formula (X1-3).

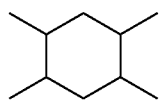
(X1-3)

In addition, the polyimide resin of the present invention contains a repeating structural unit represented by the above-mentioned general formula (2).

In the general formula (2), $X^2$ represents a tetravalent group containing an aromatic ring and having a carbon number of from 6 to 22. Having $X^2$ that contains an aromatic ring, in particular, the polyimide resin of the present invention has a low coefficient of linear thermal expansion and is excellent in transparency and has heat resistance.

$X^2$ may have at least one aromatic ring. The aromatic ring may be a monocyclic ring or a condensed ring, and the examples thereof include a benzene ring, a naphthalene ring, an anthracene ring, a tetracene ring, etc. Of those, preferred are a benzene ring and a naphthalene ring, and more preferred is a benzene ring.

The carbon number of $X^2$ is from 6 to 22, and preferably from 6 to 18, more preferably from 6 to 12.

From the viewpoint of the transparency, the heat resistance and the low coefficient of linear thermal expansion of the polyimide resin, $X^2$ is preferably at least one selected from tetravalent groups represented by the following general formulae (X2-1) to (X2-3), and is more preferably a tetravalent group represented by the general formula (X2-3).

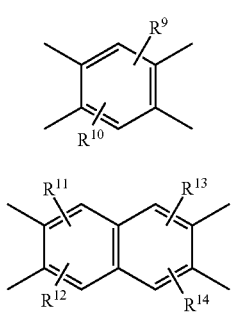
(X2-1)

(X2-2)

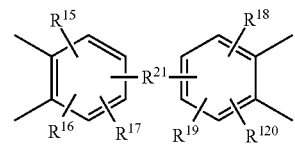
(X2-3)

$R^9$ to $R^{20}$ each independently represent a hydrogen atom, a halogen atom, an alkyl group having a carbon number of from 1 to 6, or a halogenoalkyl group. $R^{21}$ represents a single bond, —$CH_2$—, —$C(CH_3)_2$—, —O—, —S—, —$SO_2$—, —CONN—, —CO—, or —$C(CF_3)_2$—.

In the general formulae (X2-1) to (X2-3), $R^9$ to $R^{20}$ each are preferably a hydrogen atom or a methyl group, more preferably a hydrogen atom. In the general formula (X2-3), $R^{21}$ is preferably a single bond, —$CH_2$— or —$C(CH_3)_2$—, more preferably a single bond. From the viewpoint of the low coefficient of linear thermal expansion, $X^2$ is more preferably a tetravalent group represented by the following structural formula (X2-4).

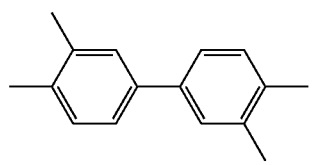
(X2-4)

In the repeating structural unit represented by the general formula (1) and the repeating structural unit represented by the general formula (2), $R^1$ and $R^2$ each independently represent a divalent organic group, which includes the divalent group represented by the structural formula (B1). Here, the content of the divalent group represented by the following structural formula (B1) relative to the total of $R^1$ and $R^2$ in the polyimide resin is from 80 to 100 mol %, and is, from the viewpoint of the transparency, the heat resistance and the low coefficient of linear thermal expansion of the resin, preferably from 85 to 100 mol %, more preferably from 90 to 100 mol %, even more preferably from 95 to 100 mol %, still more preferably from 96 to 100 mol %. When the content of the divalent group represented by the structural formula (B1) is less than 80 mol %, the transparency of the polyimide resin is liable to lower.

In the general formula (1) and the general formula (2), $R^1$ and $R^2$ may contain any other divalent organic group than the group represented by the structural formula (B1). The divalent organic group is not specifically limited, but is, from the viewpoint of the heat resistance of the resin, preferably a divalent organic group having an aromatic ring. The content of the other divalent organic group than the group represented by the structural formula (B1) is 20 mol % or less relative to the total of $R^1$ and $R^2$ in the polyimide resin.

Here, in particular, in a case where the polyimide resin of the present invention is used in a resin composition that contains silica microparticles to be mentioned hereinunder, it is desirable that the divalent organic group represented by $R^1$ and $R^2$ in the general formula (1) and the general formula (2) contains a divalent organic group having a phenolic structure. The polyimide resin that contains a divalent organic group having a phenolic structure has good affinity with silica microparticles, and therefore the dispersibility of the silica microparticles in the resin composition could be improved and the transparency of the polyimide film using the resin composition could be thereby improved.

The divalent organic group having a phenolic structure may have at least one phenolic structure but preferably has two or more phenolic structures. From the viewpoint of the transparency, the heat resistance and the low coefficient of linear thermal expansion of the polyimide resin, and from the viewpoint of the affinity of the resin with silica microparticles, it is more desirable that the divalent organic group having a phenolic structure is a divalent group represented by the following general formula (B2).

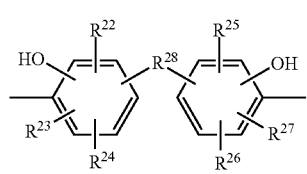
(B2)

$R^{22}$ to $R^{27}$ each independently represent a hydrogen atom, a halogen atom, a hydroxyl group, an alkyl group having a carbon number of from 1 to 6, or a halogenoalkyl group. $R^{28}$ represents a single bond, —CH$_2$—, —C(CH$_3$)$_2$—, —O—, —S—, —SO$_2$—, —CONH—, —CO—, or —C(CF$_3$)$_2$—.

In the general formula (B2), $R^{22}$ to $R^{27}$ each are preferably a hydrogen atom or a methyl group, more preferably a hydrogen atom. $R^{28}$ is preferably a single bond, —CH$_2$—, or —C(CH3)$_2$—, more preferably a single bond.

Preferably, the divalent group represented by the general formula (B2) is at least one selected from the divalent groups represented by the following structural formulae (B2-1) to (B2-5), and is, from the viewpoint of the availability of the compound, more preferably the divalent group represented by the following structural formula (B2-1).

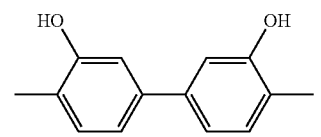
(B2-1)

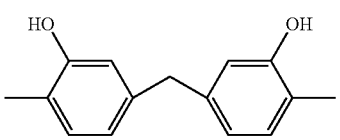
(B2-2)

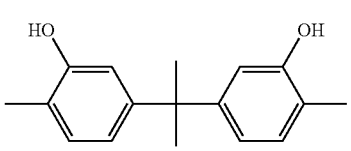
(B2-3)

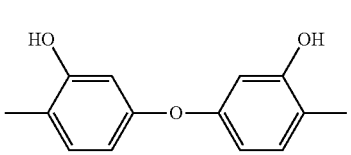
(B2-4)

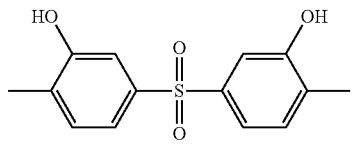
(B2-5)

The content of the divalent organic group having a phenolic structure in the polyimide resin may be, from the viewpoint of the affinity with silica microparticles, more than 0 mol % and 20 mol % or less relative to the total of $R^1$ and $R^2$ in the general formula (1) and the general formula (2). Preferably, the content is 15 mol % or less, more preferably 10 mol % or less. Also preferably, the content is 4 mol % or more, more preferably 5 mol % or more.

In the polyimide resin of the present invention, the content of the repeating structural unit represented by the general formula (2) relative to the total of the repeating structural unit represented by the general formula (1) and the repeating structural unit represented by the general formula (2) is from 35 to 75 mol %, and is, from the viewpoint of the transparency, the heat resistance and the low coefficient of linear thermal expansion, preferably from 35 to 65 mol %, more preferably from 40 to 60 mol %. When the content of the repeating structural unit represented by the general formula (2) relative to the total of the repeating structural units represented by the general formulae (1) and (2) is less than 35 mol %, the coefficient of linear thermal expansion of the resin increases. On the other hand, when the content is more than 75 mol %, the resin is liable to discolor and the transparency thereof is liable to lower. In addition, in the case, the polyimide resin production would be difficult.

The total content of the repeating structural unit represented by the general formula (1) and the repeating structural unit represented by the general formula (2) relative to all the repeating units constituting the polyimide resin of the present invention is preferably from 50 to 100 mol %, more preferably from 75 to 100 mol %, even more preferably from 90 to 100 mol %, still more preferably 100 mol %.

The number-average molecular weight of the polyimide resin of the present invention is, from the viewpoint of the mechanical strength of the polyimide film formed of the resin, preferably from 5,000 to 100,000. The number-average molecular weight of the polyimide resin can be measured through gel permeation chromatography.

Production of Polyimide Resin

The polyimide resin of the present invention can be produced by reacting a tetracarboxylic acid component with a diamine component.

The tetracarboxylic acid component includes a tetracarboxylic acid containing an alicyclic hydrocarbon structure or a derivative thereof, and a tetracarboxylic acid containing an aromatic ring or a derivative thereof. The diamine component includes a diamine represented by the following structural formula (B1').

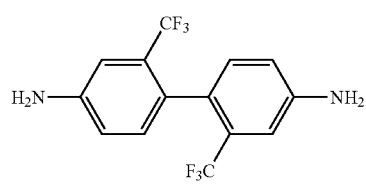
(B1')

The tetracarboxylic acid containing an alicyclic hydrocarbon structure is preferably a compound in which four carboxyl groups directly bond to the alicyclic hydrocarbon therein, and may contain an alkyl group in the structure thereof. The tetracarboxylic acid preferably has a carbon number of from 8 to 26.

Examples of the tetracarboxylic acid containing an alicyclic hydrocarbon structure include 1,2,3,4-cyclobutanetetracarboxylic acid, 1,2,4,5-cyclopentanetetracarboxylic acid, 1,2,4,5-cyclohexanetetracarboxylic acid, bicyclo[2.2.2]oct-7-ene-2,3,5,6-tetracarboxylic acid, dicyclohexyltetracarboxylic acid, and regioisomers thereof, etc.

Derivatives of the tetracarboxylic acid containing an alicyclic hydrocarbon structure include anhydrides and alkyl esters of the tetracarboxylic acid. The tetracarboxylic acid derivative is preferably one having a carbon number of from 8 to 38. Anhydrides of the tetracarboxylic acid containing an alicyclic hydrocarbon structure include 1,2,3,4-cyclobutanetetracarboxylic dianhydride, 1,2,4,5-cyclopentanetetracarboxylic dianhydride, 1,2,4,5-cyclohexanetetracarboxylic dianhydride, bicyclo[2.2.2]oct-7-ene-2,3,5,6-tetracarboxylic dianhydride, dicyclohexyltetracarboxylic dianhydride, and regioisomers thereof, etc.

Alkyl esters of the tetracarboxylic acid containing an alicyclic hydrocarbon structure are preferably those in which the carbon number of the alkyl is from 1 to 3. For example, there are mentioned dimethyl esters, diethyl esters and dipropyl esters of the above-mentioned, alicyclic hydrocarbon structure-containing tetracarboxylic acids.

As the alicyclic hydrocarbon structure-containing tetracarboxylic acid or the derivative thereof, one selected from the above may be used singly, or two or more compounds thereof may be used as combined.

Of the above-mentioned alicyclic hydrocarbon structure-containing tetracarboxylic acid components, preferred are cycloalkanetetracarboxylic acids, bicycloalkanetetracarboxylic acids and dianhydrides thereof, more preferred are cycloalkanetetracarboxylic acids having a ring carbon number of from 4 to 6, bicycloalkanetetracarboxylic acids having a ring carbon number of from 4 to 6, and dianhydrides thereof, and even more preferred are 1,2,4,5-cyclohexanetetracarboxylic acid and dianhydride thereof.

The tetracarboxylic acid containing an aromatic ring is preferably a compound in which four carboxyl groups directly bond to the aromatic ring therein, and may contain an alkyl group in the structure thereof. The tetracarboxylic acid preferably has a carbon number of from 10 to 26. The tetracarboxylic acid includes pyromellitic acid, 3,3',4,4'-diphenylsulfonetetracarboxylic acid, 3,3',4,4'-benzophenonetetracarboxylic acid, 4,4'-oxydiphthalic acid, 2,2',3,3'-benzophenonetetracarboxylic acid, 3,3',4,4'-biphenyltetracarboxylic acid, 2,2',3,3'-biphenyltetracarboxylic acid, 2,2-bis(3,4-dicarboxyphenyl)propane, 2,2-bis(2,3-dicarboxyphenyl)propane, 2,2-bis(3,4-dicarboxyphenoxyphenyl)propane, 1,1-bis(2,3-dicarboxyphenyl)ethane, 1,2-bis(2,3-dicarboxyphenyl)ethane, 1,1-bis(3,4-dicarboxyphenyl)ethane, 1,2-bis(3,4-dicarboxyphenyl)ethane, bis(2,3-dicarboxyphenyl)methane, bis(3,4-dicarboxyphenyl)methane, 4,4'-(p-phenylenedioxy)diphthalic acid, 4,4'-(m-phenylenedioxy)diphthalic acid, 2,3,6,7-naphthalenetetracarboxylic acid, 1,4,5,8-naphthalenetetracarboxylic acid, etc.

Derivatives of the tetracarboxylic acid containing an aromatic ring include anhydrides and alkyl esters of the tetracarboxylic acid. The tetracarboxylic acid derivative is preferably one having a carbon number of from 10 to 38. Anhydrides of the tetracarboxylic acid containing an aromatic ring include pyromellitic acid monoanhydride, pyromellitic acid dianhydride, 3,3',4,4'-diphenylsulfonetetracarboxylic dianhydride, 3,3',4,4'-benzophenonetetracarboxylic dianhydride, 4,4'-oxydiphthalic dianhydride, 2,2',3,3'-benzophenonetetracarboxylic dianhydride, 3,3',4,4'-biphenyltetracarboxylic dianhydride, 2,2',3,3'-biphenyltetracarboxylic dianhydride, 2,2-bis(3,4-dicarboxyphenyl)propane dianhydride, 2,2-bis(2,3-dicarboxyphenyl)propane dianhydride, 2,2-bis(3,4-dicarboxyphenoxyphenyl)propane dianhydride, 1,1-bis(2,3-dicarboxyphenyl)ethane dianhydride, 1,2-bis(2,3-dicarboxyphenyl)ethane dianhydride, 1,1-bis(3,4-dicarboxyphenyl)ethane dianhydride, 1,2-bis(3,4-dicarboxyphenyl)ethane dianhydride, bis(2,3-dicarboxyphenyl)methane dianhydride, bis(3,4-dicarboxyphenyl)methane dianhydride, 4,4'-(p-phenylenedioxy)diphthalic dianhydride, 4,4'-(m-phenylenedioxy)diphthalic dianhydride, 2,3,6,7-naphthalenetetracarboxylic dianhydride, 1,4,5,8-naphthalenetetracarboxylic dianhydride, etc.

Alkyl esters of the tetracarboxylic acid containing an aromatic ring are preferably those in which the carbon number of the alkyl is from 1 to 3. For example, there are mentioned dimethyl esters, diethyl esters and dipropyl esters of the above-mentioned, aromatic ring-containing tetracarboxylic acids.

As the aromatic ring-containing tetracarboxylic acid or the derivative thereof, one selected from the above may be used singly, or two or more compounds thereof may be used as combined.

Of the above-mentioned aromatic ring-containing tetracarboxylic acid components, preferred are one or more selected from pyromellitic acid, 2,3,5,6-toluenetetracarboxylic acid, 3,3',4,4'-biphenyltetracarboxylic acid, 1,4,5,8-naphthalenetetracarboxylic acid and dianhydrides thereof, and from the viewpoint of the transparency, the heat resistance and the low coefficient of linear thermal expansion, more preferred are 3,3',4,4'-biphenyltetracarboxylic acid and dianhydride thereof.

In producing the polyimide resin of the present invention, the amount of the aromatic ring-containing tetracarboxylic acid component to be charged relative to the total amount of the alicyclic hydrocarbon structure-containing tetracarboxylic acid component and the aromatic ring-containing tetracarboxylic acid component is from 35 to 75 mol %.

The tetracarboxylic acid component for use in the polyimide resin of the present invention may contain any other tetracarboxylic acid component not containing any of an alicyclic hydrocarbon structure and an aromatic ring, within a range not detracting from various physical properties of the polyimide resin. The tetracarboxylic acid component of the type includes 1,2,3,4-butanetetracarboxylic acid, 1,2,3,4-pentanetetracarboxylic acid, derivatives thereof, etc.

The used amount of the tetracarboxylic acid component not containing any of an alicyclic hydrocarbon structure and an aromatic ring is preferably 10 mol % or less relative to all the tetracarboxylic acid components used here, more preferably 5 mol % or less, even more preferably 1 mol % or less.

The diamine component for use in the polyimide resin of the present invention contains a diamine represented by the above-mentioned structural formula (B1'), as described above.

In producing the polyimide resin for use in a resin composition that contains silica microparticles to be described hereinunder, it is desirable that the diamine component contains a diamine having a phenolic structure. The phenolic structure-having diamine is preferably a diamine represented by the following general formula (B2'), which is capable of forming a divalent group represented by the above-mentioned general formula (B2), and more preferably 3,3'-dihydroxybenzidine, which is capable of forming the divalent group represented by the above-mentioned structural formula (B2-1).

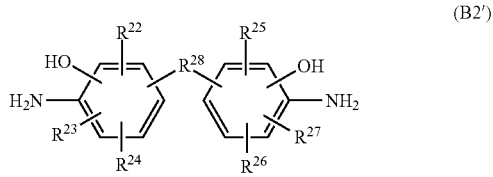

(B2')

$R^{22}$ to $R^{28}$ are the same as described above.

In producing the polyimide resin of the present invention, the amount of the diamine represented by the structural formula (B1') to be charged relative to the total amount of all the diamine components is preferably from 80 to 100 mol %. In a case where a diamine represented by the general formula (B2') is used, the amount of the diamine represented by the general formula (B2') to be charged relative to the total amount of all the diamine components is preferably more than 0 mol % and 20 mol % or less.

The diamine component for use in the polyimide resin composition of the present invention may contain any other diamine component than the diamines represented by the structural formula (B1') and the general formula (B2'), within a range not detracting from various physical properties of the polyimide resin. The other diamine is not specifically limited, and examples thereof include an aliphatic diamine, an aromatic ring-containing diamine, etc. From the viewpoint of the heat resistance of the polyimide resin, preferred are aromatic ring-containing diamines.

As the aliphatic diamine, alicyclic hydrocarbon structure-containing diamines and linear aliphatic diamines are exemplified, and for example, 1,2-bis(aminomethyl)cyclohexane, 1,3-bis(aminomethyl)cyclohexane, 1,4-bis(aminomethyl)cyclohexane, 1,2-cyclohexanediamine, 1,3-cyclohexanediamine, 1,4-cyclohexanediamine, 4,4'-diaminodicyclohexylmethane, 4,4'-methylenebis(2-methylcyclohexylamine), carbondiamine, limonenediamine, isophoronediamine, norbornanediamine, bis(aminomethyl)tricyclo[5.2.1.02,6]decane, 3,3'-dimethyl-4,4'-diaminodicyclohexylmethane, 4,4'-diaminodicyclohexylpropane, 1,5-pentamethylenediamine, 1,6-hexamethylenediamine, 1,7-heptamethylenediamine, 1,8-octamethylenediamine, 1,9-nonamethylenediamine, 1,10-decamethylenediamine, 1,11-undecamethylenediamine, 1,12-dodecamethylenediamine, 2,2'-(ethylenedioxy)bis(ethyleneamine), etc. are exemplified.

As the aromatic ring-containing diamine, exemplified are orthoxylylenediamine, metaxylylenediamine, paraxylylenediamine, 1,2-diethynylbenzenediamine, 1,3-diethynylbenzenediamine, 1,4-diethynylbenzenediamine, 1,2-diaminobenzene, 1,3-diaminobenzene, 1,4-diaminobenzene, 4,4'-diaminodiphenyl ether, 3,4'-diaminodiphenyl ether, 4,4'-diaminodiphenyl methane, α,α'-bis(4-aminophenyl)-1,4-diisopropylbenzene, α,α'-bis(3-aminophenyl)-1,4-diisopropylbenzene, 2,2-bis[4-(4-aminophenoxy)phenyl]propane, 2,6-diaminonaphthalene, 1,5-diaminonaphthalene, 4,4'-diaminobenzanilide, 3,4'-diaminobenzanilide, etc.

One alone or two or more of the above-mentioned diamine components may be used here either singly or as combined.

The used amount of the other diamine component is 20 mol % or less relative to all the diamine components, preferably 10 mol % or less, more preferably 5 mol % or less, even more preferably 1 mol % or less.

In producing the polyimide resin of the present invention, the amount ratio of the tetracarboxylic acid component and the diamine component to be charged is preferably such that the amount of the diamine component is from 0.9 to 1.1 mol relative to 1 mol of the tetracarboxylic acid component.

In producing the polyimide resin of the present invention, a terminal blocking agent may be used in addition to the above-mentioned tetracarboxylic acid components and the above-mentioned diamine component. The terminal blocking agent is preferably a monoamine or a dicarboxylic acid. The charged amount of the terminal blocking agent to be introduced is preferably from 0.0001 to 0.1 mol relative to 1 mol of the tetracarboxylic acid component, more preferably from 0.001 to 0.06 mol. As the monoamine terminal blocking agent, for example, recommended are methylamine, ethylamine, propylamine, butylamine, benzylamine, 4-methylbenylamine, 4-ethylbenzylamine, 4-dodecylbenzylamine, 3-methylbenzylamine, 3-ethylbenzylamine, aniline, 3-methylaniline, 4-methylaniline, etc. Of those, preferred for use herein are benzylamine and aniline. As the dicarboxylic acid terminal blocking agent, preferred are dicarboxylic acids, which may be partially ring-closed. For example, recommended are phthalic acid, phthalic anhydride, 4-chlorophthalic acid, tetrafluorophthalic acid, 2,3-benzophenonedicarboxylic acid, 3,4-benzophenonedicarboxylic acid, cyclohexane-1,2-dicarboxylic acid, cyclopentane-1,2-dicarboxylic acid, 4-cyclohexene-1,2-dicarboxylic acid, etc. Of those, preferred for use herein are phthalic acid and phthalic anhydride.

The method for reacting the above-mentioned tetracarboxylic acid component with the above-mentioned diamine component is not specifically limited, for which employable is any known method.

As specific reaction methods, there are mentioned (1) a method which includes putting a tetracarboxylic acid component, a diamine component and a reaction solvent into a reactor, stirring them at room temperature to 80° C. for 0.5 to 30 hours, and thereafter heating them for imidation, (2) a method which includes putting a diamine component and a reaction solvent into a reactor and dissolving it in the solvent, then adding thereto a tetracarboxylic acid component, stirring them at room temperature to 80° C. for 0.5 to 30 hours, and thereafter heating them for imidation, (3) a method which includes putting a tetracarboxylic acid component, a diamine component and a reaction solvent into a reactor, and then immediately heating them for imidation, and the like.

The reaction solvent for use for production of the polyimide resin may be any one capable of dissolving the produced polyimide resin, not detracting from the imidation reaction. For example, there are exemplified an aprotic solvent, a phenolic solvent, an ether solvent, a carbonate solvent, etc.

Specific examples of the aprotic solvent include amide solvents such as N,N-dimethylformamide, N,N-dimethylacetamide, N-methyl-2-pyrrolidone, N-methylcaprolactam, 1,3-dimethylimidazolidinone, tetramethylurea, etc.; lactone solvents such as γ-butyrolactone, γ-valerolactone, etc.; phosphorus-containing amide solvents such as hexamethylphosphoric amide, hexamethylphosphine triamide, etc.; sulfur-containing solvents such as dimethyl sulfone, dimethyl sulfoxide, sulfolane, etc.; ketone solvents such as acetone, cyclohexane, methylcyclohexane, etc.; amine solvents such as picoline, pyridine, etc.; ester solvents such as (2-methoxy-1-methylethyl) acetate, etc.

Specific examples of the phenolic solvent include phenol, o-cresol, m-cresol, p-cresol, 2,3-xylenol, 2,4-xylenol, 2,5 xylenol, 2,6-xylenol, 3,4-xylenol, 3,5-xylenol, etc.

Specific examples of the ether solvent include 1,2-dimethoxyethane, bis(2-methoxyethyl) ether, 1,2-bis(2-methoxyethoxy)ethane, bis[2-(2-methoxyethoxy)ethyl] ether, tetrahydrofuran, 1,4-dioxane, etc.

Specific examples of the carbonate solvent include diethyl carbonate, methylethyl carbonate, ethylene carbonate, propylene carbonate, etc.

Of those reaction solvents, preferred are an amide solvent and a lactone solvent. One alone or two or more of these reaction solvents may be used here either singly or as combined.

In the imidation, preferably, a Dean Stark apparatus or the like is used for removing water formed during the production process. Such an operation increases the degree of polymerization and the imidation ratio.

Any known imidation catalyst may be used in the imidation. As the imidation catalyst, a base catalyst and an acid catalyst are exemplified.

The base catalyst includes organic base catalysts such as pyridine, quinoline, isoquinoline, α-picoline, β-picoline, 2,4-lutidine, 2,6-lutidine, trimethylamine, triethylamine, tripropylamine, tributylamine, imidazole, N,N-dimethylaniline, N,N-diethylaniline, etc.; and inorganic base catalysts such as potassium hydroxide, sodium hydroxide, potassium carbonate, sodium carbonate, potassium hydrogencarbonate, sodium hydrogencarbonate, etc.

The acid catalyst includes crotonic acid, acrylic acid, trans-3-hexenoic acid, cinnamic acid, benzoic acid, methylbenzoic acid, oxybenzoic acid, terephthalic acid, benzenesulfonic acid, paratoluenesulfonic acid, naphthalenesulfonic acid, etc. One alone or two or more of these imidation catalysts may be used here either singly or as combined.

Of the above, preferred is use of base catalysts from the viewpoint of the handleability thereof, more preferred is use of organic base catalysts, and even more preferred is use of triethylamine.

The temperature of the imidation is preferably from 120 to 250° C., more preferably from 160 to 190° C., from the viewpoint of the reactivity and preventing gelation. Also preferably, the reaction time after the start of distillation of the produced water is from 0.5 to 10 hours.

Polyamide Acid

The present invention also provides a polyamide acid that is a precursor of the polyimide resin. The precursor of the polyimide resin means a polyamide acid that is before imidation to obtain the polyimide resin.

The polyimide resin of the present invention generally soluble in an organic solvent, but depending on the structure thereof, the solubility of the polyimide resin in an organic solvent may be low. In such a case, from the viewpoint of the handleability and the processability, a composition containing a polyamide acid that is a precursor of the polyimide resin (that is, a polyamide acid composition to be mentioned below) may be formed into desired shapes such as films or the like, and then may be subjected to the above-mentioned imidation.

The polyamide acid of the present invention contains a repeating structural unit represented by the following general formula (3) and a repeating structural unit represented by the following general formula (4), in which the content of the repeating structural unit represented by the general formula (4) relative to the total of the repeating structural unit represented by the general formula (3) and the repeating structural unit represented by the general formula (4) is from 35 to 75 mol %, preferably from 35 to 65 mol %, even more preferably from 40 to 60 mol %. The other preferred embodiments of the acid are the same as those of the polyimide resin.

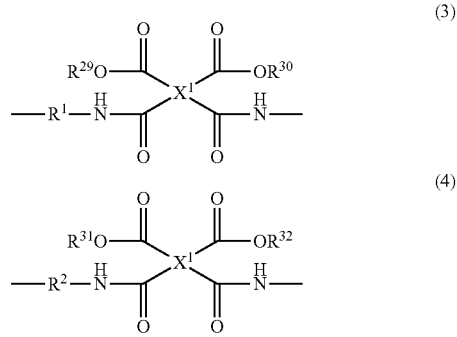

$X^1$, $X^2$, $R^1$ and $R^2$ are the same as those mentioned above. $R^{29}$ to $R^{32}$ each independently represent a hydrogen atom or an alkyl group, preferably a hydrogen atom or an alkyl group having a carbon number of from 1 to 3.

The polyamide acid can be obtained by reacting the above-mentioned tetracarboxylic acid component with the above-mentioned diamine component. The method for the reaction is not specifically limited, for which employable is any known method.

As specific reaction methods, there are mentioned (1) a method which includes putting a tetracarboxylic acid component, a diamine component and a solvent into a reactor, and stirring them at 0 to 120° C., preferably at 5 to 80° C. for 1 to 72 hours, (2) a method which includes putting a diamine component and a solvent into a reactor and dissolving it in the solvent, then adding thereto a tetracarboxylic acid component, and stirring them at 0 to 120° C., preferably at 5 to 80° C. for 1 to 72 hours, and the like. Of the above, preferred is the production method (2).

In the case of reaction at 80° C. or lower, the molecular weight of the resultant polyamide acid does not fluctuate depending on the temperature history in polymerization and in the case, in addition, thermal imidation can be prevented and therefore the polyamide acid can be produced stably.

The solvent for use for production of the polyamide acid may be any one capable of dissolving the produced polyamide acid. For example, there are exemplified N-methyl-2-pyrrolidone, N,N-dimethylacetamide, N,N-dimethylformamide, γ-butyrolactone, γ-valerolactone, dimethyl sulfoxide, 1,4-dioxane, cyclohexanone, etc. One alone or two or more of these solvents may be used here either singly or as combined.

In the above-mentioned production method (1), a solution prepared by dissolving a diamine component and a tetracarboxylic acid component in the above-mentioned solvent is stirred in a temperature range of from 0 to 120° C., preferably from 5 to 80° C. for 1 to 72 hours to obtain a solution containing a polyamide acid. In the production method (2), while a solution prepared by dissolving a diamine component in the above-mentioned solvent is stirred, a tetracarboxylic acid component is gradually added thereto and stirred in a temperature range of from 0 to 120° C., preferably from 5 to 80° C. for 1 to 72 hours to obtain a solution containing a polyamide acid.

The concentration of the polyamide acid in the resultant polyamide acid solution is, from the viewpoint of using the solution as a polyamide acid composition, generally within a range of from 1 to 50% by mass in the polyamide acid solution, preferably from 3 to 35% by mass, more preferably from 10 to 30% by mass.

The polyamide acid composition contains the polyamide acid produced in the manner as above. Using the polyamide acid composition also gives the polyimide resin of the present invention. The polyamide acid composition is favorably used especially for forming polyimide films.

From the viewpoint of efficiently attaining the imidation, it is desirable that the polyamide acid composition further contains an imidation catalyst and a dehydration catalyst. The imidation catalyst may be any one having a boiling point of 40° C. or higher and 180° C. or lower, but preferred is an amine compound having a boiling point of 180° C. or lower. The imidation catalyst having a boiling point of 180° C. or lower may be free from the risk of discoloration of the formed films in drying at high temperatures and the appearance of the films could be prevented from being worsened. On the other hand, the imidation catalyst having a boiling point of 40° C. or higher can be prevented from being evaporated away before the end of sufficient imidation.

The amine compound that is used favorable as the imidation catalyst includes pyridine and picoline. One alone or two or more such imidation catalysts may be used here either singly or as combined.

The dehydration catalyst includes acid anhydrides such as acetic anhydride, propionic anhydride, n-butyric anhydride, benzoic anhydride, trifluoroacetic anhydride, etc.; carbodiimide compounds such as dicyclohexylcarbodiimide, etc. One alone or two or more of these may be used here either singly or as combined.

The polyamide acid composition may contain additives such as antioxidant, a light stabilizer, a surfactant, a flame retardant, a plasticizer, etc., within a range not detracting from the effects of the present invention. Silica microparticles to be mentioned below may also be incorporated in the polyamide acid composition.

By subjecting the polyamide acid composition to heating and dehydrating for ring closure, the polyimide resin of the present invention can be obtained.

The heating temperature can be selected from a range of generally from 100 to 400° C., preferably from 200 to 350° C., more preferably from 250 to 300° C. The heating time is generally from 1 minute to 6 hours, preferably from 5 minutes to 2 hours, more preferably from 15 minutes to 1 hour.

The heating atmosphere may be air gas, nitrogen gas, oxygen gas, hydrogen gas, nitrogen/hydrogen mixed gas, etc. For the purpose of preventing the resultant polyimide resin from being discolored, preferred is a nitrogen gas having an oxygen concentration of 100 ppm or less, or a nitrogen/hydrogen mixed gas having a hydrogen concentration of 0.5% or less.

Regarding the method for producing a polyimide film using the polyamide acid composition, for example, the polyamide acid composition is coated onto a glass substrate or the like, then heated, dried and dehydrated for ring closure thereon based on the above-mentioned condition, and thereafter the resultant film is obtained by peeling away from the substrate. The coating method with the polyamide acid composition is not specifically limited, for which employable is any known method.

The thickness of the polyimide film produced using the polyamide acid composition is generally from 0.1 to 500 μm, preferably from 1 to 250 μm, more preferably from 5 to 100 μm, even more preferably from 10 to 50 μm.

Resin Composition

The resin composition of the present invention contains the polyimide resin of the present invention and silica microparticles. Even when used alone, the polyimide resin of the present invention is excellent in heat resistance and has a low coefficient of linear thermal expansion, but when the polyimide resin of the present invention is applied to a resin composition containing silica microparticles, the composition can give a polyimide film having a further lower coefficient of linear thermal expansion.

The polyimide resin for use in the resin composition of the present invention is the same as above. From the viewpoint of the affinity with silica microparticles, the polyimide resin preferably contains repeating structural units represented by the general formulae (1) and (2) where the divalent organic group represented by $R^1$ and $R^2$ contains a divalent organic group having a phenolic structure. In the case, the content of the phenolic structure-having divalent organic group may be more than 0 mol % and 20 mol % or less relative to the total of $R^1$ and $R^2$, and is preferably 15 mol % or less, more preferably 10 mol % or less. The content is preferably 4 mol % or more, more preferably 5 mol % or more. Preferred examples of the phenolic structure-having divalent organic group are the same as mentioned above.

Silica Microparticles

Silica for the silica microparticles for use herein is silicon dioxide ($SiO_2$), and the morphology (crystalline morphology, amorphousness, etc.) thereof is not limited. The shape of the silica microparticles is not also limited, and examples thereof include spherical, oval, flat, rod-shaped, fibrous and the like ones.

The silica microparticles for use in the present invention preferably have a small particle size, from the viewpoint of realizing high light transmittance of the resin composition and the polyimide film, and the mean particle size thereof is preferably from 1 to 100 nm, more preferably from 1 to 50 nm, even more preferably from 5 to 25 nm.

The mean particle size of the silica microparticles can be measured, for example, according to a BET method.

The silica microparticles may be surface-treated with a surface-treating agent such as a silane coupling agent or the like, from the viewpoint of the dispersibility thereof in the polyimide resin.

Any known silane coupling agent may be used. From the viewpoint of the affinity with the polyimide resin, preferred is an amino group-containing silane coupling agent. Examples of the amino group-containing silane coupling agent include 3-(2-aminoethylamino)propyldimethoxymethylsilane, 3-(2-aminoethylamino)propyltrimethoxysilane, 3-(2-aminoethylamino)propyltriethoxysilane, 3-(3-aminopropylamino)propyltriethoxysilane, 3-(3-aminopropylamino)propyltrimethoxysilane, 3-aminopropyldiethoxymethylsilane, 3-aminopropyltriethoxysilane, 3-aminopropyltrimethoxysilane, etc. One alone or two or more of these may be used here either singly or as combined.

The surface-treating method for the silica microparticles with a silane coupling agent is not specifically limited, for which employable is any known method. For example, silica microparticles are dispersed in an organic solvent or the like to prepare a dispersion, and the above-mentioned silane coupling agent is added thereto, and stirred at a temperature falling between room temperature and 80° C. or so for several hours. A small amount of water may be added to the system to promote the treating reaction.

The ratio by mass of the polyimide resin and the silica microparticles in the resin composition of the present invention is preferably from 20/80 to 95/5, more preferably from 25/75 to 70/30, even more preferably from 35/65 to 65/35. When the ratio by mass of the polyimide resin is 20 or more, the flexibility of the polyimide film produced using the resin composition is good. When the ratio by mass of the polyimide resin is 95 or less, the resulting resin composition and the polyimide film are excellent in heat resistance and have a low coefficient of linear thermal expansion.

The resin composition of the present invention may contain any other additive than the above-mentioned polyimide resin and silica microparticles, within a range not detracting from the effects of the present invention. For example, the composition may contain an antioxidant, a light stabilizer, a surfactant, a flame retardant, a plasticizer, any other polymer compound than the above-mentioned polyimide resin, etc.

The method for preparing the resin composition of the present invention is not specifically limited, for which employable is any known method. For example, there is exemplified a method which includes adding an alkoxysilane or polyalkoxysilane to a polyimide resin solution, adding thereto a small amount of a hydrolysis accelerator such as water or the like, and dispersing silica microp articles in the solution according to a sol-gel method. A powder of silica microparticles produced as a colloidal silica according to a vapor-phase method may be directly added to the polyimide resin solution and mixed to prepare the composition.

As one preferred example for preparing the resin composition of the present invention, there is mentioned a method which includes mixing a polyimide resin solution and an organosilica sol to prepare the resin composition.

Organosilica sol is one prepared by dispersing silica microparticles in an organic solvent in a proportion of 20% by mass or so. The organic solvent to be a dispersion medium for silica microparticles is preferably a good solvent for the polyimide resin, and methanol, isopropanol, ethylene glycol, methyl ethyl ketone, N-methyl-2-pyrrolidone, N,N-dimethylformamide, N,N-dimethylacetamide, etc. are exemplified, and N-methyl-2-pyrrolidone, N,N-dimethylformamide, and N,N-dimethylacetamide are preferred.

The solid concentration in the resin composition of the present invention may be suitably selected in accordance with the processability of the composition in forming polyimide films and laminates to be mentioned below. The solid concentration and the viscosity of the composition may be suitably controlled by adding an organic solvent thereto. The organic solvent is not specifically limited as Ion as it is capable of dissolving the polyimide resin, and the same organic solvents exemplified hereinabove as the dispersion medium for silica microparticles can be exemplified.

Polyimide Film

The polyimide film of the present invention contains the polyimide resin of the present invention, and is excellent in transparency and heat resistance and has a low coefficient of linear thermal expansion.

The method for forming the polyimide film of the present invention is not specifically limited, for which employable is any known method. For example, there is mentioned a method which includes forming the polyimide resin solution of the present invention containing an organic solvent or the resin composition of the present invention containing the polyimide resin and silica microparticles into a film by coating or shaping, and thereafter removing the organic solvent. Alternatively, the polyimide film may be formed using the polyamide acid composition mentioned above.

The thickness of the polyimide film of the present invention may be suitably selected in accordance with the intended use thereof. In general, the thickness falls within a range of from 0.1 to 500 but preferably from 1 to 250 µm, more preferably from 5 to 100 µm, even more preferably from 10 to 50 µm.

The total light transmittance of the polyimide film of the present invention is preferably 85% or more, when the thickness thereof is 30 µm. The total light transmittance is more preferably 88% or more, even more preferably 89% or more.

The coefficient of linear thermal expansion of the polyimide film of the present invention is preferably 50 ppm/° C. or less, more preferably 40 ppm/° C. or less. The glass transition temperature of the polyimide film is preferably 300° C. or higher, more preferably 320° C. or higher, even more preferably 350° C. or higher.

The total light transmittance, the coefficient of linear thermal expansion and the glass transition temperature of polyimide film can be measured specifically according to the methods described in the section of Examples.

Laminate

The present invention also provides a laminate having a substrate selected from plastic film, silicon wafer, metal foil and glass, and a polyimide resin layer containing the polyimide resin of the present invention. The laminate of the present invention may have at least one polyimide resin layer, and may have two or more polyimide resin layers.

The substrate to constitute the laminate of the present invention is selected from plastic film, silicon wafer, metal foil and glass.

The resin to constitute the plastic film includes, for example, polyolefins such as homopolymers or copolymers of ethylene, propylene, isobutene, etc.; amorphous polyolefins such as cyclic polyolefins, etc.; polyesters such as polyethylene terephthalate, polyethylene-2,6-naphthalate, etc.; polyamides such as nylon 6, nylon 66, nylon 12, copolymer nylon, etc.; polyvinyl alcohol, ethylene-vinyl acetate copolymer partial hydrolyzate (EVOH), polyimide, polyether imide, polysulfone, polyether sulfone, polyether ether ketone, polycarbonate, polyarylate, fluororesin, acrylic resin; biodegradable resins such as polylactic acid, etc. Of those, preferred are polyethylene-2,6-naphthalate, polyimide, polyether imide, polysulfone, polyether sulfone and polycarbonate, from the viewpoint of the heat resistance and the dimensional stability of the laminate.

As the metal which constitutes the metal foil, any metal may be used as long as it has electroconductivity. Examples thereof include gold, silver, copper, iron and nickel. Of those, preferred is silver or copper, and more preferred is copper.

Of the above-mentioned substrate, the substrate is preferably a metal foil, more preferably a copper foil.

The thickness of the substrate may be suitably selected in accordance with the intended use of the laminate, and is preferably from 0.1 to 500 μm, more preferably from 1 to 250 μm.

The polyimide resin layer to constitute the laminate of the present invention contains at least the polyimide resin of the present invention. The thickness of the polyimide resin layer may be suitably selected in accordance with the intended use of the laminate, and is preferably from 0.5 to 50 μm, more preferably from 1 to 30 μm. In a case where the laminate of the present invention has two or more polyimide resin layers, the thickness of the polyimide resin layer means the total thickness of all the resin layers.

The production method for the laminate of the present invention is not specifically limited, for which employable is any known method. For example, there may be mentioned a method which includes applying the polyimide resin solution of the present invention containing an organic solvent, the polyamide acid composition or the resin composition of the present invention containing the polyimide resin and silica microparticles onto a substrate, followed by removing the organic solvent.

The polyimide film that contains the polyimide resin of the present invention is favorably used as films for various members such as color filters, flexible displays, semiconductor components, optical members, etc. The laminate of the present invention is also favorably used as a substrate for printed-wiring assemblies.

EXAMPLES

The present invention is described more specifically with reference to Examples given below. However, the present invention is not whatsoever limited by these Examples.

The films produced in Examples and Comparative Examples were evaluated as follows:

(1) Total Light Transmittance

The total light transmittance was measured using a color/turbidity coincidence measuring instrument (COH 400) manufactured by Nippon Denshoku Industries Co., Ltd.

(2) Coefficient of Linear Thermal Expansion (CTE)

Using a thermal mechanical analyzer (TMA/SS 6100) manufactured by SIT Nano Technology Inc., TMA measurement was carried out under the condition of a heating rate of 10° C./min to measure CTE in the range of from 100 to 200° C.

(3) Glass Transition Temperature

Using a differential scanning thermometer (DSC 6200) manufactured by SII Nano Technology Inc., DSC measurement was carried out under the condition of a heating rate of 10° C./min to measure the glass transition temperature.

Production Example 1

Synthesis of 1,2,4,5-cyclohexanetetracarboxylic dianhydride 552 g of pyromellitic acid, 200 g of a catalyst of rhodium held on active carbon (manufactured by N.E. Chemcat Corporation), and 1656 g of water were put into a hastelloy (HC22) autoclave having an inner volume of 5 liters, and while stirring, the reactor was purged with nitrogen gas. Next, the reactor was purged with hydrogen gas so that the hydrogen pressure in the reactor could be 5.0 MPa, and heated up to 60° C. While the hydrogen pressure was kept at 5.0 MPa, this was reacted for 2 hours. The hydrogen gas in the reactor was purged with nitrogen gas, and the reaction liquid was taken out of the autoclave. The reaction liquid was filtered at a hot state to separate the catalyst from a filtrate. The filtrate was concentrated by evaporating water under reduced pressure with a rotary evaporator, thereby precipitating a crystal. The precipitated crystal was separated through solid-liquid separation at room temperature and dried to obtain 481 g of 1,2,4,5-cyclohexanetetracarboxylic acid (yield 85.0%).

Subsequently, 450 g of the resultant 1,2,4,5-cyclohexanetetracarboxylic acid and 4000 g of acetic anhydride were put into a 5-liter separable glass flask (equipped with a Dimroth condenser), and while stirring, the reactor was purged with nitrogen gas. This was heated up to the reflux temperature of the solvent under the nitrogen gas atmosphere, and the solvent was refluxed for 10 minutes. While stirring, this was cooled to room temperature to precipitate a crystal. The precipitated crystal was separated through solid-liquid separation and dried to obtain a primary crystal. Further, the separated mother liquid was concentrated under reduced pressure using a rotary evaporator to precipitate a crystal. The crystal was separated through solid-liquid separation and dried to obtain a secondary crystal. The primary crystal and the secondary crystal were combined to obtain 375 g of 1,2,4,5-cyclohexanetetracarboxylic dianhydride (yield in anhydration, 96.6%).

Example 1

In a nitrogen stream atmosphere, 14.565 g (0.045 mol) of 2,2'-bis(trifluoromethyl)benzidine, and, as a solvent, 62.42 g of γ-butyrolactone and 26.75 g of N,N-dimethylacetamide were put into a 500-mL five-neck flask equipped with a thermometer, a stirrer, a nitrogen-introducing duct, a side tube-having dropping funnel, a Dean Stark unit and a condenser, and dissolved therein. 4.075 g (0.018 mol) of 1,2,4,5-cyclohexanetetracarboxylic dianhydride synthesized in Production Example 1 and 8.027 g (0.027 mol) of 3,3',4,4'-biphenyltetracarboxylic dianhydride and, as an imidation catalyst, 0.92 g (0.05 mol) of triethylamine were added thereto all at a time. After the addition, this was heated up to 170° C., and refluxed for 5 hours while the distillate was removed as needed. The finish of water distillation was confirmed, and this was cooled to 120° C. 135.82 g of N,N-dimethylacetamide was added thereto, and stirred and mixed for 2 hours to obtain a polyimide resin solution.

Subsequently, the resultant polyimide resin solution was applied onto a glass plate, and held on a hot plate at 100° C. for 60 minutes to remove the organic solvent through evaporation, thereby giving a self-supporting colorless transparent primary-dried film. The film was fixed on a stainless frame, and heated in a hot air drier at 250° C. for 2 hours to evaporate the solvent thereby giving a film having a thickness of 30 μm. The evaluation results are shown in Table 1.

Example 2

In a nitrogen stream atmosphere, 14.752 g (0.046 mol) of 2,2'-bis(trifluoromethyl)benzidine, and, as a solvent, 62.20 g of γ-butyrolactone were put into a 500-mL five-neck flask equipped with a thermometer, a stirrer, a nitrogen-introducing duct, a side tube-having dropping funnel, a Dean Stark unit and a condenser, and dissolved therein, and then 5.159 g (0.023 mol) of 1,2,4,5-cyclohexanetetracarboxylic dianhydride synthesized in Production Example 1 and 6.775 g (0.023 mol) of 3,3',4,4'-biphenyltetracarboxylic dianhydride and, as an imidation catalyst, 1.16 g (0.05 mol) of triethylamine were added thereto all at a time. After the dropwise addition, this was heated up to 170° C., and refluxed for 5 hours while the distillate was removed as needed. The finish of water distillation was confirmed, and this was cooled to 120° C. 162.8 g of N,N-dimethylacetamide was added thereto, and stirred and mixed for 2 hours to obtain a polyimide resin solution.

Subsequently, the resultant polyimide resin solution was applied onto a glass plate, and held on a hot plate at 100° C. for 60 minutes to remove the organic solvent through evaporation, thereby giving a self-supporting colorless transparent primary-dried film. The film was fixed on a stainless frame, and heated in a hot air drier at 250° C. for 2 hours to evaporate the solvent, thereby giving a film having a thickness of 30 µm. The evaluation results are shown in Table 1.

Example 3

In a nitrogen stream atmosphere, 14.945 g (0.047 mol) of 2,2'-bis(trifluoromethyl)benzidine, and, as a solvent, 62.25 g of γ-butyrolactone were put into a 500-mL five-neck flask equipped with a thermometer, a stirrer, a nitrogen-introducing duct, a side tube-having dropping funnel, a Dean Stark unit and a condenser, and dissolved therein, and then 6.272 g (0.028 mol) of 1,2,4,5-cyclohexanetetracarboxylic dianhydride synthesized in Production Example 1 and 5.491 g (0.019 mol) of 3,3',4,4'-biphenyltetracarboxylic dianhydride and, as an imidation catalyst, 1.41 g (0.05 mol) of triethylamine were added thereto all at a time. After the dropwise addition, this was heated up to 170° C., and refluxed for 5 hours while the distillate was removed as needed. The finish of water distillation was confirmed, and this was cooled to 120° C. 162.75 g of N,N-dimethylacetamide was added thereto, and stirred and mixed for 2 hours to obtain a polyimide resin solution.

Subsequently, the resultant polyimide resin solution was applied onto a glass plate, and held on a hot plate at 100° C. for 60 minutes to remove the organic solvent through evaporation, thereby giving a self-supporting colorless transparent primary-dried film. The film was fixed on a stainless frame, and heated in a hot air drier at 250° C. for 2 hours to evaporate the solvent thereby giving a film having a thickness of 30 The evaluation results are shown in Table 1.

Example 4

In a nitrogen stream atmosphere, 13.536 g (0.042 mol) of 2,2'-bis(trifluoromethyl)benzidine, 1.018 g (0.005 mol) of 3,3'-dihydroxybenzidine and, as a solvent, 49.82 g of γ-butyrolactone and 12.46 g of N,N-dimethylacetamide were put into a 500-mL five-neck flask equipped with a thermometer, a stirrer, a nitrogen-introducing duct, a side tube-having dropping funnel, a Dean Stark unit and a condenser, and dissolved therein, and then 5.260 g (0.023 mol) of 1,2,4,5-cyclohexanetetracarboxylic dianhydride synthesized in Production Example 1 and 6.907 g (0.023 mol) of 3,3',4,4'-biphenyltetracarboxylic dianhydride and, as an imidation catalyst, 1.19 g (0.05 mol) of triethylamine were added thereto all at a time. After the dropwise addition, this was heated up to 170° C., and refluxed for 5 hours while the distillate was removed as needed. The finish of water distillation was confirmed, and this was cooled to 60° C. 125 g of a dispersion of silica microparticles, DMAC-ST (mean particle size 11 nm, content of silica microparticles 20% by mass, N,N-dimethylacetamide solution: manufactured by Nissan Chemical Industries, Ltd.) were added thereto, and stirred and mixed for 2 hours to obtain a polyimide resin composition containing a polyimide resin and silica microparticles.

Subsequently, the resultant polyimide resin composition was applied onto a glass plate, and held on a hot plate at 100° C. for 60 minutes to remove the organic solvent through evaporation, thereby giving a self-supporting colorless transparent primary-dried film. The film was fixed on a stainless frame, and heated in a hot air drier at 250° C. for 2 hours to evaporate the solvent thereby giving a film having a thickness of 30 µm. The evaluation results are shown in Table 1.

Example 5

A film having a thickness of 30 µm was produced according to the same method as in Example 4 except that silica microparticles were not used therein. The evaluation results are shown in Table 1.

Comparative Example 1

In a nitrogen stream atmosphere, 22.714 g (0.071 mol) of 2,2'-bis(trifluoromethyl)benzidine, and, as a solvent, 74.38 g of γ-butyrolactone were put into a 500-mL five-neck flask equipped with a thermometer, a stirrer, a nitrogen-introducing duct, a side tube-having dropping funnel, a Dean Stark unit and a condenser, and dissolved therein, and then 11.121 g (0.050 mol) of 1,2,4,5-cyclohexanetetracarboxylic dianhydride synthesized in Production Example 1 and 6.259 g (0.021 mol) of 3,3',4,4'-biphenyltetracarboxylic dianhydride and, as an imidation catalyst, 2.51 g (0.05 mol) of triethylamine were added thereto all at a time. After the dropwise addition, this was heated up to 170° C., and refluxed for 5 hours while the distillate was removed as needed. The finish of water distillation was confirmed, and this was cooled to 120° C. 138.12 g of N,N-dimethylacetamide was added thereto and stirred and mixed for 2 hours to obtain a polyimide resin solution.

Subsequently, the resultant polyimide resin solution was applied onto a glass plate, and held on a hot plate at 100° C. for 60 minutes to remove the organic solvent through evaporation, thereby giving a self-supporting colorless transparent primary-dried film. The film was fixed on a stainless frame, and heated in a hot air drier at 250° C. for 2 hours to evaporate the solvent thereby giving a film having a thickness of 30 µm. The evaluation results are shown in Table 1.

Comparative Example 2

In a nitrogen stream atmosphere, 16.225 g (0.039 mol) of 2,2-bis[4-(4-aminophenoxy)phenyl]propane, and, as a solvent, 61.65 g of γ-butyrolactone were put into a 500-mL five-neck flask equipped with a thermometer, a stirrer, a nitrogen-introducing duct, a side tube-having dropping funnel, a Dean Stark unit and a condenser, and dissolved therein, and then 4.424 g (0.020 mol) of 1,2,4,5-cyclohexanetetracarboxylic dianhydride synthesized in Production Example 1 and 5.810 g (0.020 mol) of 3,3',4,4'-biphenyltetracarboxylic dianhydride and, as an imidation catalyst, 1.00 g (0.05 mol) of triethylamine were added thereto all at a time. After the dropwise addition, this was heated up to 170° C., and refluxed for 5 hours while the distillate was removed as needed. The finish of water distillation was confirmed, and this was cooled to 120° C. 163.35 g of N,N-dimethylacetamide was added thereto and stirred and mixed for 2 hours to obtain a polyimide resin solution.

Subsequently, the resultant polyimide resin solution was applied onto a glass plate, and held on a hot plate at 100° C. for 60 minutes to remove the organic solvent through evaporation, thereby giving a self-supporting colorless transparent primary-dried film. The film was fixed on a stainless frame, and heated in a hot air drier at 250° C. for 2 hours to evaporate the solvent thereby giving a film having a thickness of 30 μm. The evaluation results are shown in Table 1.

Comparative Example 3

In a nitrogen stream atmosphere, 17.509 g (0.034 mol) of 2,2-bis[4-(4-aminophenoxy)phenyl]hexafluoropropane, and, as a solvent, 61.17 g of γ-butyrolactone were put into a 500-mL five-neck flask equipped with a thermometer, a stirrer, a nitrogen-introducing duct, a side tube-having dropping funnel, a Dean Stark unit and a condenser, and dissolved therein, and then 3.780 g (0.017 mol) of 1,2,4,5-cyclohexanetetracarboxylic dianhydride synthesized in Production Example 1 and 4.964 g (0.017 mol) of 3,3',4,4'-biphenyltetracarboxylic dianhydride and, as an imidation catalyst, 0.85 g (0.05 mol) of triethylamine were added thereto all at a time. After the dropwise addition, this was heated up to 170° C., and refluxed for 5 hours while the distillate was removed as needed. The finish of water distillation was confirmed, and this was cooled to 120° C. 163.83 g of N,N-dimethylacetamide was added thereto and stirred and mixed for 2 hours to obtain a polyimide resin solution.

Subsequently, the resultant polyimide resin solution was applied onto a glass plate, and held on a hot plate at 100° C. for 60 minutes to remove the organic solvent through evaporation, thereby giving a self-supporting colorless transparent primary-dried film. The film was fixed on a stainless frame, and heated in a hot air drier at 250° C. for 2 hours to evaporate the solvent thereby giving a film having a thickness of 30 μm. The evaluation results are shown in Table 1.

Comparative Example 4

Synthesis of a polyimide resin was tried according to the same method as in Example 1 except that, in Example 1, the amount of 1,2,4,5-cyclohexanetetracarboxylic dianhydride synthesized in Production Example 1 was changed to 2.108 g (0.009 mol) and the amount of 3,3',4,4'-biphenyltetracarboxylic dianhydride was changed to 10.592 g (0.036 mol). However, during the synthesis operation, a solid precipitated and a polyimide resin solution could not be obtained.

TABLE 1

| | Composition of Polyimide Film | | | | | |
|---|---|---|---|---|---|---|
| | Composition of Polyimide Resin (molar ratio in terms of charged amount) | | | | | Content of Formula (2) relative to Total of Unit |
| | Tetracarboxylic Acid Component (X1) | Tetracarboxylic Acid Component (X2) | Diamine Component (B1') | Diamine Component (B2') | Other Diamine Component | of Formula (1) and Unit of Formula (2) (mol %)*1 |
| Example 1 | HPMDA 40 | BPDA 60 | TFMB 100 | — | — | 60 |
| Example 2 | HPMDA 50 | BPDA 50 | TFMB 100 | — | — | 50 |
| Example 3 | HPMDA 60 | BPDA 40 | TFMB 100 | — | — | 40 |
| Example 4 | HPMDA 50 | BPDA 50 | TFMB 90 | HAB 10 | — | 50 |
| Example 5 | HPMDA 50 | BPDA 50 | TFMB 90 | HAB 10 | — | 50 |
| Comparative Example 1 | HPMDA 70 | BPDA 30 | TFMB 100 | — | — | 30 |
| Comparative Example 2 | HPMDA 50 | BPDA 50 | — | — | BAPP 100 | 50 |
| Comparative Example 3 | HPMDA 50 | BPDA 50 | — | — | HFBAPP 100 | 50 |
| Comparative Example 4 | HPMDA 20 | BPDA 80 | TFMB 100 | — | — | 80 |

| | Composition of Polyimide Film | | Evaluation Results | | |
|---|---|---|---|---|---|
| | Content of Structural Formula (B1) relative to Total of $R^1$ and $R^2$ (mol %)*2 | Polyimide Resin/Silica Microparticle (ratio by mass) | Total Light Transmittance (%) | Coefficient of Linear Thermal Expansion (ppm/° C.) | Glass Transition Temperature (° C.) |
| Example 1 | 100 | — | 89.5 | 33 | 368 |
| Example 2 | 100 | — | 89.8 | 39 | 360 |
| Example 3 | 100 | — | 91.0 | 44 | 354 |
| Example 4 | 90 | 50/50 | 91.2 | 28 | 357 |

TABLE 1-continued

| | | | | | |
|---|---|---|---|---|---|
| Example 5 | 90 | — | 89.7 | 39 | 351 |
| Comparative Example 1 | 100 | — | 91.6 | 51 | 342 |
| Comparative Example 2 | 0 | — | 90.0 | 56 | 294 |
| Comparative Example 3 | 0 | — | 89.4 | 57 | 295 |
| Comparative Example 4 | 100 | — | | | |

*1 calculated from the molar amount of the tetracarboxylic acid component charged.
*2 calculated from the molar amount of the diamine component charged.

The abbreviations in the Table are as follows:
HPMDA: 1,2,4,5-cyclohexanetetracarboxylic dianhydride
BPDA: 3,3',4,4'-biphenyltetracarboxylic dianhydride
TFMB: 2,2'-bis(trifluoromethyl)benzidine
HAB: 3,3'-dihydroxybenzidine
BAPP: 2,2-bis[4-(4-aminophenoxy)phenyl]propane
HFBAPP: 2,2-bis[4-(4-aminophenoxy)phenyl]hexafluoropropane As shown in Table 1, the polyimide films of Examples each containing the polyimide resin of the present invention have good transparency and a high glass transition temperature and have a low coefficient of linear thermal expansion.

As opposed to these, in the polyimide film of Comparative Example 1, the content of the repeating structural unit represented by the general formula (2) relative to the total of the repeating structural unit represented by the general formula (1) and the repeating structural unit represented by the general formula (2) in the polyimide resin is less than 35 mol %, and therefore, the film has a low glass transition temperature and a high coefficient of linear thermal expansion. In the polyimide films of Comparative Examples 2 and 3, the polyimide resin does not contain a divalent group represented by the structural formula (B1), and therefore the films has a low glass transition temperature and a high coefficient of linear thermal expansion, and the transparency thereof therefore lowers.

INDUSTRIAL APPLICABILITY

The polyimide film containing the polyimide resin of the present invention is excellent in transparency and heat resistance and has a low coefficient of linear thermal expansion, and is therefore favorable for films for components that are required to have dimensional stability. For example, the film is expected to be used in color filters, flexible displays, semiconductor components, optical members and the like. In addition, the laminate of the present invention is favorably used as a substrate for printed-wiring assemblies, etc.

The invention claimed is:

1. A polyimide resin comprising a repeating structural unit represented by the following formula (1) and a repeating structural unit represented by the following formula (2), wherein the content of the repeating structural unit represented by the formula (2) relative to the total of the repeating structural unit represented by the formula (1) and the repeating structural unit represented by the formula (2) is from 35 to 75 mol %:

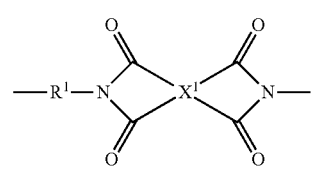

(1)

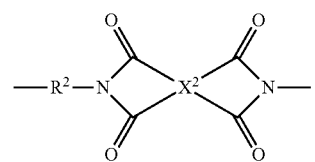

(2)

wherein $X^1$ represents a tetravalent group comprising an alicyclic hydrocarbon structure and having a carbon number of from 4 to 22; $X^2$ represents a tetravalent group comprising an aromatic ring and having a carbon number of from 6 to 22; $R^1$ and $R^2$ each independently represent a divalent organic group, and the content of the divalent group represented by the following structural formula (B1) relative to the total of $R^1$ and $R^2$ is from 80 to 90 mol %:

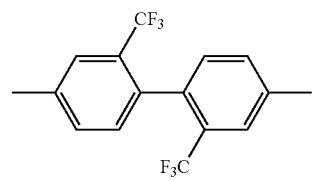

(B1)

wherein the repeating structural unit represented by formula (1) and the repeating structural unit represented by formula (2) contains a divalent organic group having a phenolic structure as the divalent organic group represented by $R^1$ and $R^2$.

2. The polyimide resin according to claim 1, wherein the content of the repeating structural unit represented by the formula (2) relative to the total of the repeating structural unit represented by the formula (1) and the repeating structural unit represented by the formula (2) is from 35 to 65 mol %.

3. The polyimide resin according to claim 1, wherein $X^1$ represents at least one selected from tetravalent groups represented by the following formulae (X1-1) and (X1-2):

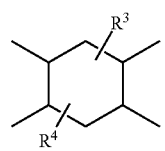

(X1-1)

-continued (X1-2)

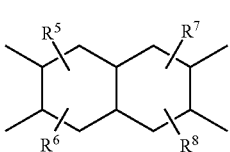

wherein $R^3$ to $R^8$ each independently represent a hydrogen atom, a halogen atom, an alkyl group having a carbon number of from 1 to 6, or a halogenoalkyl group.

4. The polyimide resin according to claim 3, wherein $X^1$ is a tetravalent group represented by the formula (X1-1).

5. The polyimide resin according to claim 1, wherein $X^2$ is at least one selected from tetravalent groups represented by the following formulae (X2-1) to (X2-3):

(X2-1)

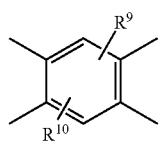

(X2-2)

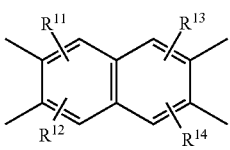

(X2-3)

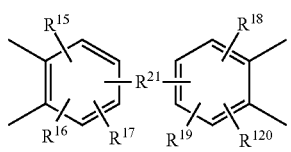

wherein $R^9$ to $R^{20}$ each independently represent a hydrogen atom, a halogen atom, an alkyl group having a carbon number of from 1 to 6, or a halogenoalkyl group, and $R^{21}$ represents a single bond, —$CH_2$—, —$C(CH_3)_2$—, —O—, —S—, —$SO_2$—, —CONH—, —CO—, or —$C(CF_3)_2$—.

6. The polyimide resin according to claim 5, wherein $X^2$ is a tetravalent group represented by the following structural formula (X2-4):

(X2-4)

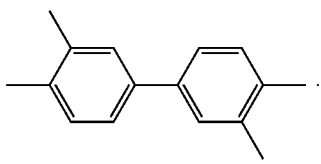

7. The polyimide resin according to claim 1, wherein the divalent organic group having a phenolic structure is a divalent group represented by the following formula (B2):

(B2)

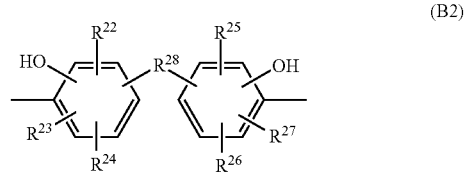

wherein $R^{22}$ to $R^{27}$ each independently represent a hydrogen atom, a halogen atom, a hydroxyl group, an alkyl group having a carbon number of from 1 to 6, or a halogenoalkyl group; $R^{28}$ represents a single bond, —$CH_2$—, —$C(CH_3)_2$—, —O—, —S—, —$SO_2$—, —CONH—, —CO—, or —$C(CF_3)_2$—.

8. The polyimide resin according to claim 1, wherein the content of the divalent organic group having a phenolic structure in the polyimide resin is more than 0 mol % and 20 mol % or less, relative to the total of $R^1$ and $R^2$ in the formula (1) and the formula (2).

9. A polyamide acid that is a precursor of the polyimide resin of claim 1.

10. A resin composition comprising the polyimide resin of claim 1 and silica microparticles.

11. The resin composition according to claim 10, wherein the content ratio by mass of the polyimide resin to the silica microparticles is from 20/80 to 95/5.

12. The resin composition according to claim 10, wherein the mean particle size of the silica microparticles is from 1 to 100 nm.

13. A polyimide film comprising the polyimide resin of claim 1.

14. The polyimide film according to claim 13, which has a total light transmittance of 85% or more when the film polyimide has a thickness of 30 μm.

15. A laminate comprising a substrate selected from plastic film, silicon wafer, metal foil and glass, and a polyimide resin layer containing the polyimide resin of claim 1.

16. The laminate according to claim 15, wherein the substrate is copper foil.

17. The polyimide resin according to claim 7, wherein the content of the divalent organic group having a phenolic structure in the polyimide resin is more than 0 mol % and 20 mol % or less, relative to the total of $R^1$ and $R^2$ in the formula (1) and the formula (2).

18. The resin composition according to claim 11, wherein the mean particle size of the silica microparticles is from 1 to 100 nm.

* * * * *